United States Patent
Follmer

(10) Patent No.: US 11,284,913 B2
(45) Date of Patent: Mar. 29, 2022

(54) APPARATUS, SYSTEM, AND METHOD FOR VASCULATURE OBSTRUCTION REMOVAL

(71) Applicant: Progressive NEURO, Inc., Santa Clara, CA (US)

(72) Inventor: Brett Allen Follmer, Santa Clara, CA (US)

(73) Assignee: Progressive NEURO, Inc.

( * ) Notice: Subject to any disclaimer, the term of this patent is extended or adjusted under 35 U.S.C. 154(b) by 80 days.

(21) Appl. No.: 16/736,279

(22) Filed: Jan. 7, 2020

(65) Prior Publication Data

US 2020/0214728 A1 Jul. 9, 2020

Related U.S. Application Data

(60) Provisional application No. 62/789,584, filed on Jan. 8, 2019.

(51) Int. Cl.
*A61B 17/221* (2006.01)
*A61B 17/00* (2006.01)

(52) U.S. Cl.
CPC .. *A61B 17/221* (2013.01); *A61B 2017/00358* (2013.01); *A61B 2017/00778* (2013.01)

(58) Field of Classification Search
CPC ........ A61F 2/0108; A61F 2/01; A61F 2/0103; A61F 2/0105; A61F 2/011; A61F 2/012; A61F 2/013; A61F 2/014; A61F 2002/015; A61F 2002/016; A61F 2002/018; A61B 17/221; A61B 2017/00358; A61B 2017/00778; A61B 17/22031; A61B 17/320725; A61B 2017/220325; A61B 2017/22038; A61B 2017/2212; A61B 2017/2215; A61B 2017/2217

USPC ........................................ 606/127, 159, 200
See application file for complete search history.

(56) References Cited

U.S. PATENT DOCUMENTS

| 4,886,061 | A | | 12/1989 | Fischell et al. |
| 4,926,858 | A | | 5/1990 | Gifford, III et al. |
| 5,772,674 | A | | 6/1998 | Nakhjavan |
| 5,935,139 | A | * | 8/1999 | Bates ................... A61B 17/221 606/159 |

(Continued)

OTHER PUBLICATIONS

International Search Report dated Mar. 30, 2020 for PCT/US2020/012528.

*Primary Examiner* — Wade Miles
*Assistant Examiner* — Kankindi Rwego
(74) *Attorney, Agent, or Firm* — Nasr Patent Law LLC; Faisal K. Abou-Nasr

(57) ABSTRACT

In embodiments of an obstruction removal device, system, and/or method, a removal tool is disposed at a distal end of a delivery tool and configured to at least partially separate an obstruction from an inner surface of a vasculature. An expandable member is also coupled to the delivery tool. The expandable member includes a proximal end that is free or slidably coupled to the delivery tool. The proximal end of the expandable member is configured to invert or slide toward a distal end of the expandable member, thereby causing the expandable member to surround at least a portion of the obstruction and the removal tool so that the obstruction is captured between the expandable member and the removal tool, when the delivery tool is withdrawn from the vasculature to remove the removal tool and the obstruction from the vasculature.

11 Claims, 12 Drawing Sheets

(56) References Cited

U.S. PATENT DOCUMENTS

| | | | |
|---|---|---|---|
| 6,001,118 A * | 12/1999 | Daniel | A61B 17/22031 606/200 |
| 6,210,370 B1 | 4/2001 | Chi-Sing et al. | |
| 6,309,399 B1 | 10/2001 | Barbut et al. | |
| 6,800,085 B2 | 10/2004 | Selmon et al. | |
| 7,041,117 B2 | 5/2006 | Suon et al. | |
| 8,608,754 B2 | 12/2013 | Wensel et al. | |
| 8,777,976 B2 | 7/2014 | Brady et al. | |
| 8,801,748 B2 | 8/2014 | Martin | |
| 8,986,241 B2 | 3/2015 | Evans et al. | |
| 9,125,728 B2 | 9/2015 | Angel et al. | |
| 9,149,609 B2 | 10/2015 | Ansel et al. | |
| 9,597,171 B2 | 3/2017 | Shrivastava et al. | |
| 9,833,252 B2 | 12/2017 | Sepetka et al. | |
| 9,987,028 B2 | 6/2018 | Lowinger et al. | |
| 10,070,878 B2 | 9/2018 | Ma | |
| 10,076,347 B2 | 9/2018 | Sepetka et al. | |
| 10,143,482 B2 | 12/2018 | Nguyen et al. | |
| 10,172,633 B2 | 1/2019 | Martin et al. | |
| 10,231,751 B2 | 3/2019 | Sos | |
| 10,271,863 B2 | 4/2019 | Marks et al. | |
| 10,314,600 B2 | 6/2019 | Morsi | |
| 10,383,644 B2 | 8/2019 | Molaei et al. | |
| 2002/0072765 A1 * | 6/2002 | Mazzocchi | A61F 2/0105 606/200 |
| 2007/0191866 A1 | 8/2007 | Palmer et al. | |
| 2009/0198269 A1 | 8/2009 | Hannes et al. | |
| 2010/0131000 A1 | 5/2010 | DeMello et al. | |
| 2010/0249815 A1 | 9/2010 | Jantzen et al. | |
| 2011/0060359 A1 | 3/2011 | Hannes et al. | |
| 2011/0213403 A1 * | 9/2011 | Aboytes | A61F 2/013 606/194 |
| 2013/0006284 A1 | 1/2013 | Aggerholm et al. | |
| 2014/0257245 A1 | 9/2014 | Rosenbluth et al. | |
| 2015/0265299 A1 | 9/2015 | Cooper et al. | |
| 2015/0342613 A1 * | 12/2015 | Aboytes | A61B 90/39 606/200 |
| 2016/0331506 A1 * | 11/2016 | Korkuch | A61F 2/013 |
| 2016/0361077 A1 | 12/2016 | Marks et al. | |
| 2017/0325830 A1 | 11/2017 | Martin et al. | |
| 2018/0008393 A1 | 1/2018 | Volobuyev et al. | |
| 2018/0036028 A1 | 2/2018 | Krolik et al. | |
| 2018/0206865 A1 | 7/2018 | Martin et al. | |
| 2018/0221037 A1 | 8/2018 | Martin et al. | |
| 2018/0256177 A1 | 9/2018 | Cooper et al. | |
| 2018/0325647 A1 | 11/2018 | Hauser | |
| 2019/0000492 A1 | 1/2019 | Casey et al. | |
| 2019/0014121 A1 | 1/2019 | Martin | |
| 2019/0125396 A1 | 5/2019 | Avneri et al. | |
| 2019/0239905 A1 | 8/2019 | Olson et al. | |
| 2019/0298396 A1 | 10/2019 | Gamba et al. | |
| 2019/0314606 A1 | 10/2019 | di Palma et al. | |

* cited by examiner

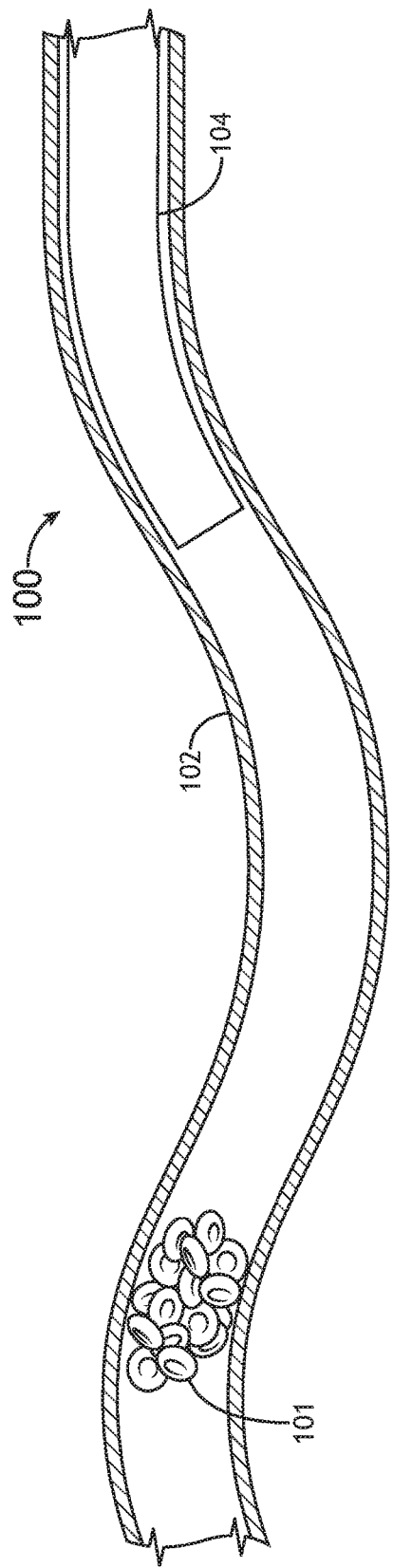
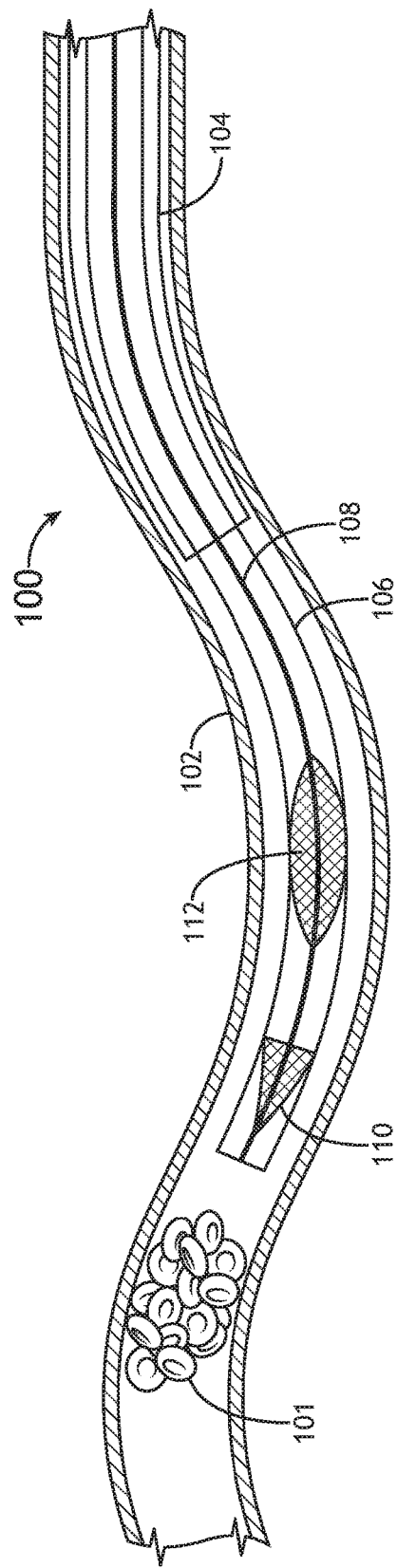

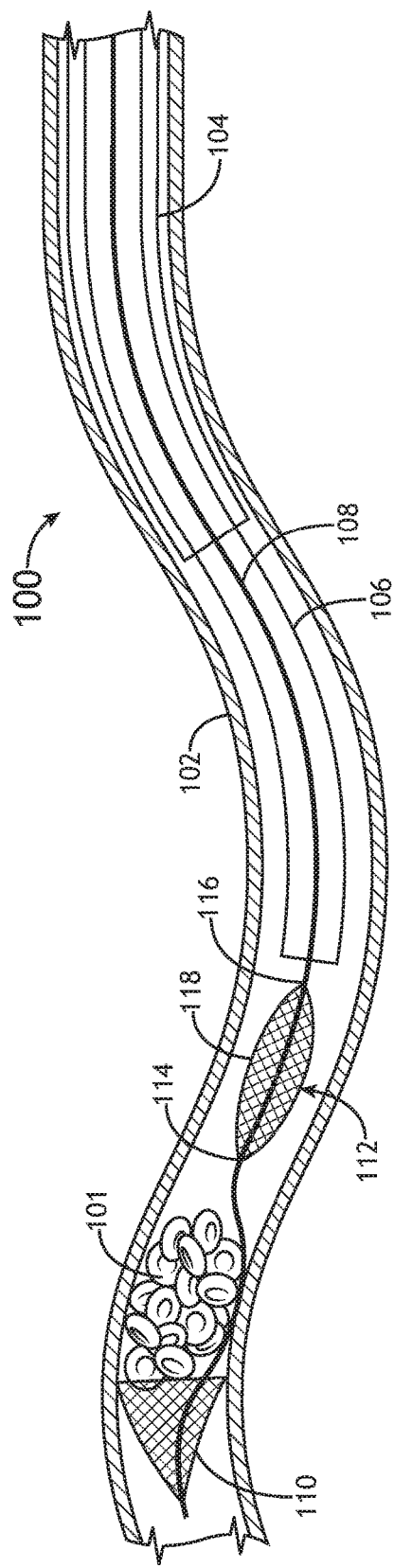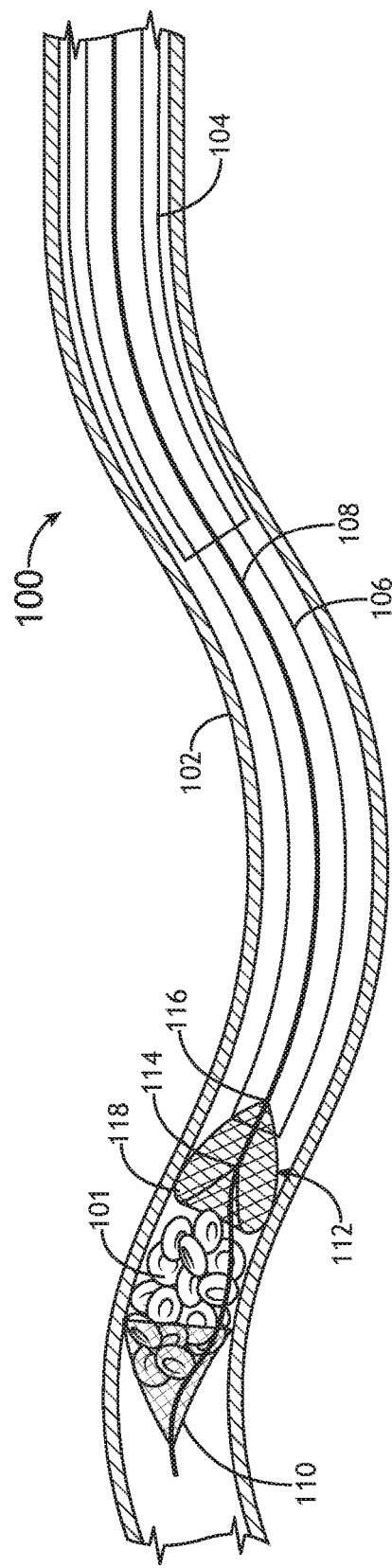
FIG.1C
FIG.1D

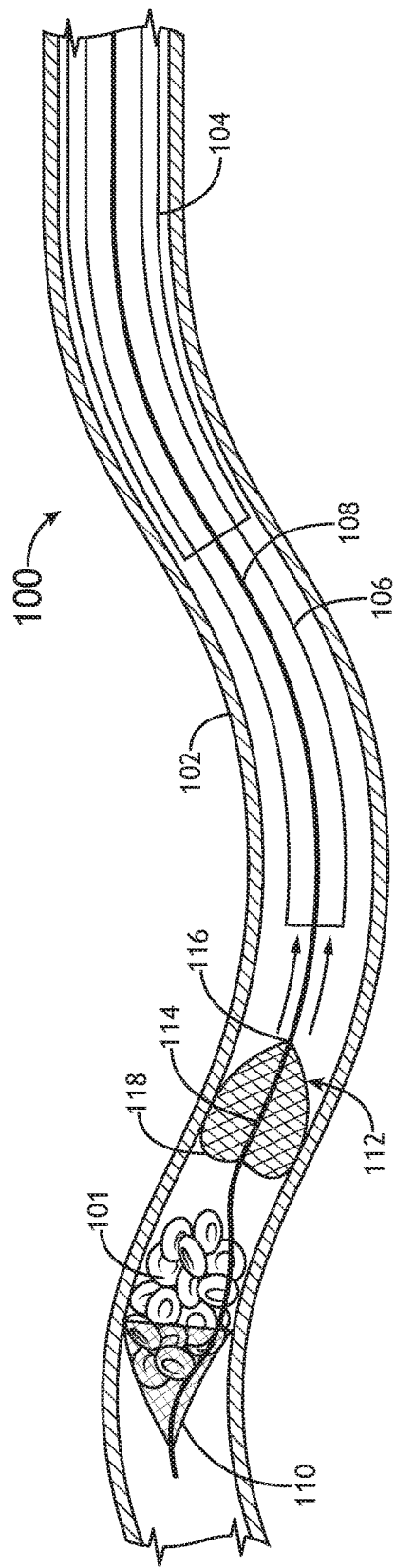
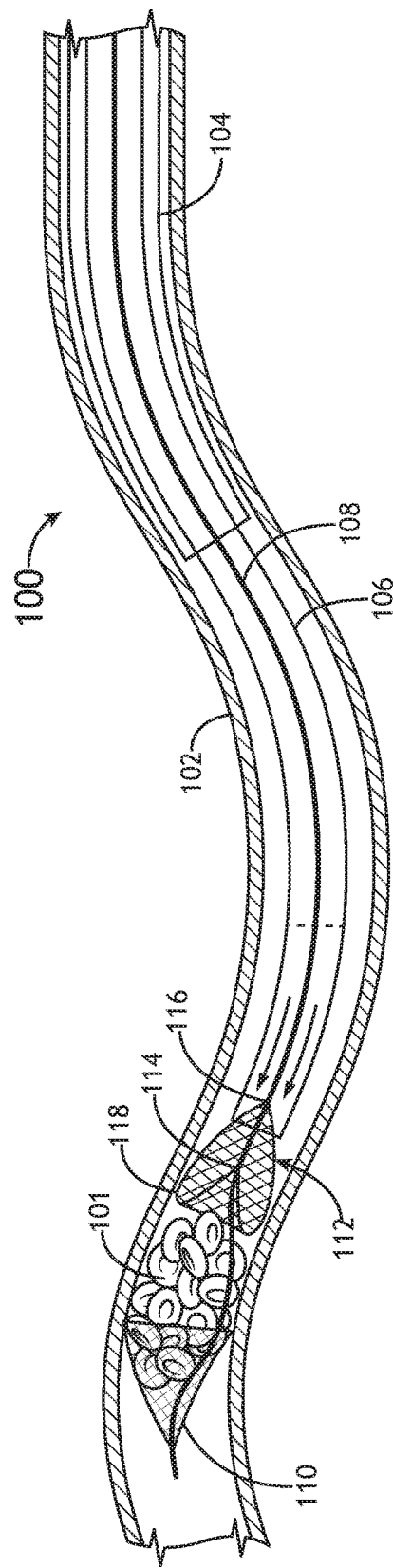
FIG.1D-1
FIG.1D-2

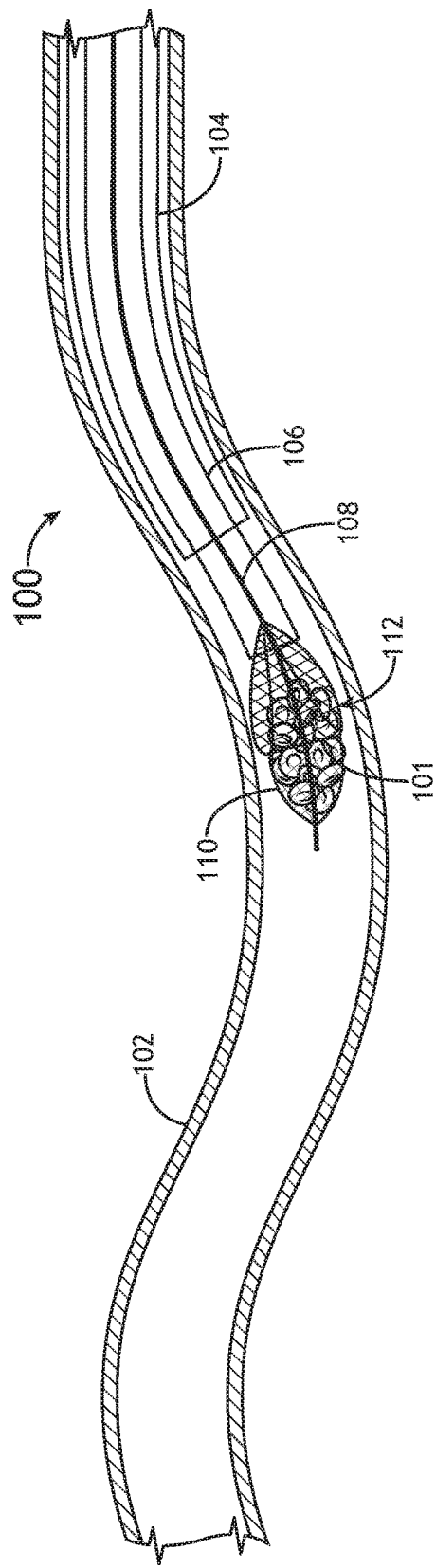
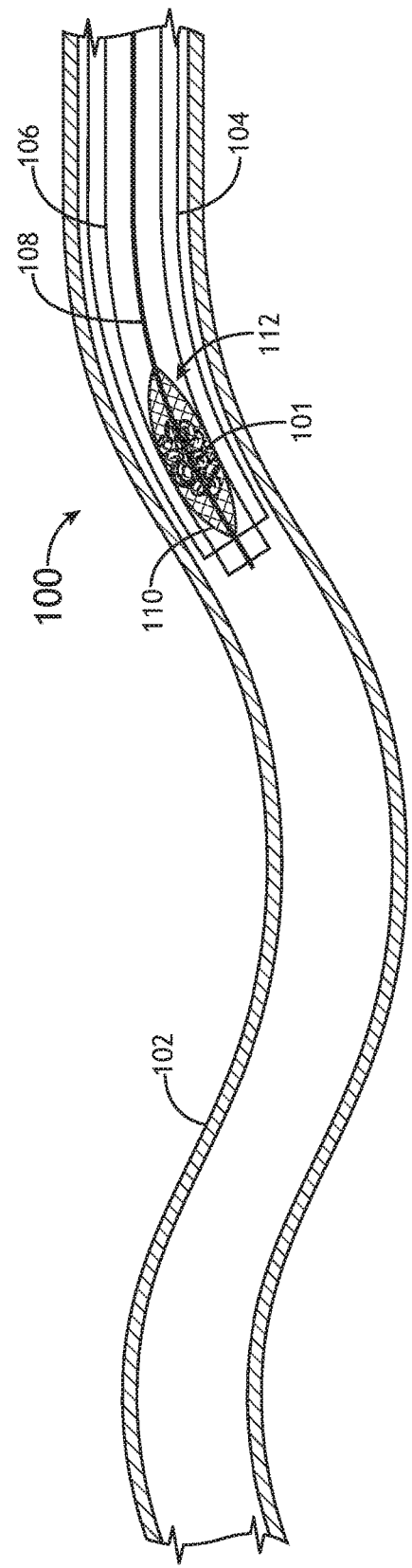
FIG.1E
FIG.1F

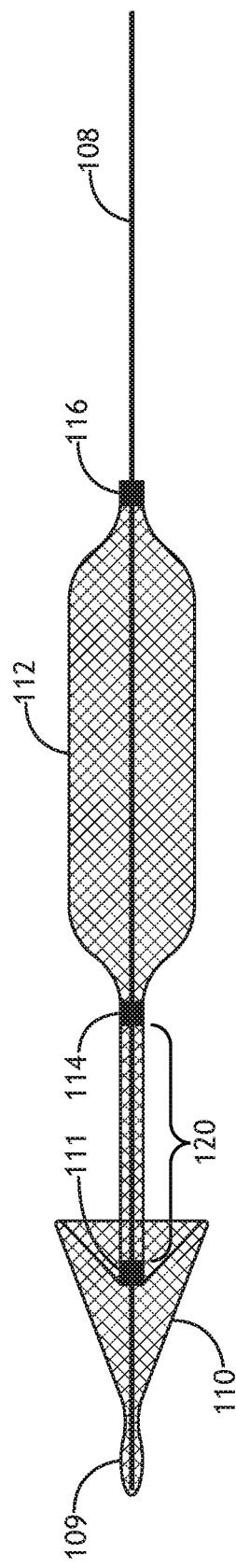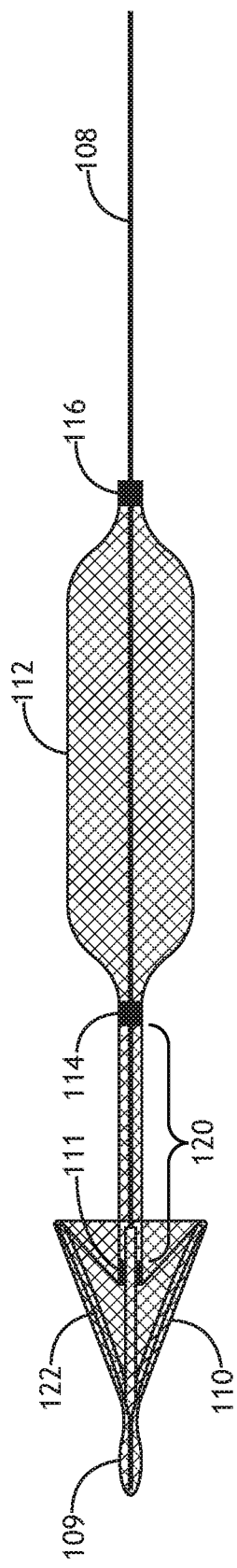
FIG. 3A
FIG. 3B

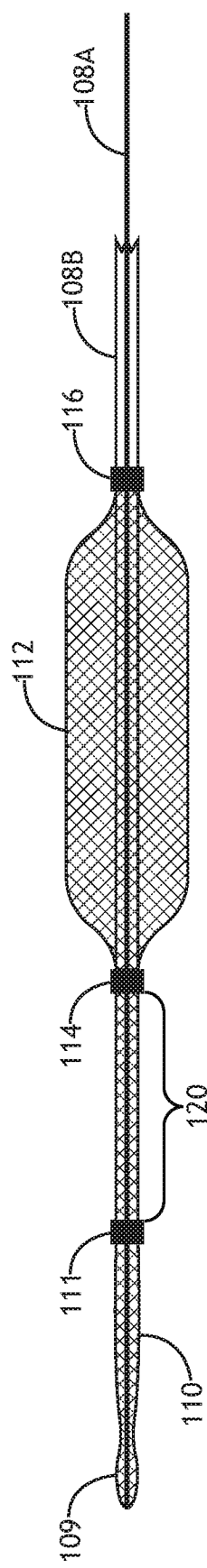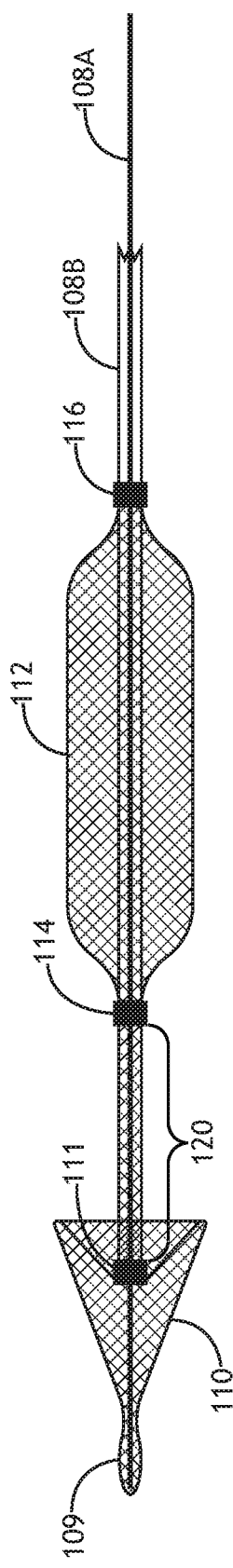
FIG. 4A
FIG. 4B

APPARATUS, SYSTEM, AND METHOD FOR VASCULATURE OBSTRUCTION REMOVAL

CROSS-REFERENCE TO RELATED APPLICATION

The present application claims the benefit under 35 U.S.C. § 119(e) of U.S. Provisional Application Ser. No. 62/789,584, filed Jan. 8, 2019, and titled "APPARATUS, SYSTEM, AND METHOD FOR VASCULATURE OBSTRUCTION REMOVAL," which is incorporated herein by reference in its entirety.

TECHNICAL FIELD

The present invention generally relates to medical devices, and, more particularly, to medical devices for removing vascular obstructions.

BACKGROUND

Obstruction removal systems/devices may operate by lodging the obstruction in a component of the removal system. In some cases, the obstruction may dislodge. Dislodgement of the obstruction substantially increases the risk for potential complications, such as stroke or heart attack. Thus, it is desirable to secure the obstruction safely for removal from the body.

SUMMARY

An obstruction removal system is disclosed. In one or more embodiments, the obstruction removal system includes a guide catheter configured to be inserted within a vasculature and a delivery tool having a distal end configured to be inserted within the guide catheter and disposed proximate to an obstruction in the vasculature. The obstruction removal system further includes a removal tool disposed at the distal end of the delivery tool. The removal tool is configured to at least partially separate an obstruction from an inner surface of a vasculature. An expandable member is also coupled to the delivery tool. The expandable member includes a proximal end that is free or slidably coupled to the delivery tool. The proximal end of the expandable member is configured to invert or slide toward a distal end of the expandable member, thereby causing the expandable member to surround at least a portion of the obstruction and the removal tool so that the obstruction is captured between the expandable member and the removal tool, when the delivery tool is withdrawn from the vasculature to remove the removal tool and the obstruction from the vasculature.

More generally, an obstruction removal device is disclosed. In one or more embodiments, the obstruction removal device includes a removal tool disposed at a distal end of a delivery tool and configured to at least partially separate an obstruction from an inner surface of a vasculature. The obstruction removal device also includes an expandable member coupled to the delivery tool. The expandable member includes a proximal end that is free or slidably coupled to the delivery tool. The proximal end of the expandable member is configured to invert or slide toward a distal end of the expandable member, thereby causing the expandable member to surround at least a portion of the obstruction and the removal tool so that the obstruction is captured between the expandable member and the removal tool, when the delivery tool is withdrawn from the vasculature to remove the removal tool and the obstruction from the vasculature.

A method for removing an obstruction from a vasculature is also disclosed. In one or more embodiments, the method includes the steps of: inserting a guide catheter within the vasculature; extending a delivery tool through the guide catheter so that a distal end of the delivery tool is disposed proximate to the obstruction in the vasculature; removing at least a portion of the obstruction in the vasculature with a removal tool disposed at the distal end of the delivery tool, wherein the removal tool is configured to at least partially separate the obstruction from an inner surface of the vasculature; and surrounding at least a portion of the obstruction and the removal tool with an expandable member coupled to the delivery tool, the expandable member including a proximal end that is free or slidably coupled to the delivery tool, wherein the proximal end of the expandable member is configured to invert or slide toward a distal end of the expandable member, so that the obstruction is captured between the expandable member and the removal tool, when the delivery tool is withdrawn from the vasculature to remove the removal tool and the obstruction from the vasculature.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

FIG. 1A illustrates a cross-sectional side view of a guide catheter of an obstruction removal system deployed within a vasculature, in accordance with one or more embodiments of the present disclosure.

FIG. 1B illustrates a cross-sectional side view of an obstruction removal device of the obstruction removal system deployed through the guide catheter, wherein the obstruction removal device includes a removal tool and an expandable member attached to a delivery tool that is fed through the guide catheter using an intermediate catheter, in accordance with one or more embodiments of the present disclosure.

FIG. 1C illustrates a cross-sectional side view of the obstruction removal device of the obstruction removal system deployed within the vasculature, wherein the intermediate catheter is pulled back (and/or the delivery tool is pushed forward) to unsheathe the obstruction removal device so that the obstruction removal device can engage the obstruction with the removal tool to at least partially separate the obstruction from an inner surface of the vasculature, in accordance with one or more embodiments of the present disclosure.

FIG. 1D illustrates a cross-sectional side view of the obstruction removal device of the obstruction removal system deployed within the vasculature, wherein a proximal end of the expandable member is being slid toward a distal end of the expandable member, and wherein a middle portion of the expandable member is being folded over the distal end of the expandable member and at least a portion of the removal tool, so that the obstruction is captured between the expandable member and the removal tool, as the delivery tool is being removed from the vasculature to remove the removal tool and the obstruction from the vasculature, in accordance with one or more embodiments of the present disclosure.

FIG. 1D-1 illustrates a cross-sectional side view of the obstruction removal device of the obstruction removal system deployed within the vasculature, wherein a proximal end of the expandable member is being slid toward a distal end of the expandable member, and wherein a middle portion of the expandable member is being folded over the distal end of the expandable member and at least a portion of the removal tool, so that the obstruction is captured between the expandable member and the removal tool, as the delivery tool is being removed from the vasculature to remove the removal tool and the obstruction from the vasculature, wherein the friction between the expandable member and the inner surface of the vasculature causes the expandable member to invert and/or fold over itself, in accordance with one or more embodiments of the present disclosure.

FIG. 1D-2 illustrates a cross-sectional side view of the obstruction removal device of the obstruction removal system deployed within the vasculature, wherein a proximal end of the expandable member is being slid toward a distal end of the expandable member, and wherein a middle portion of the expandable member is being folded over the distal end of the expandable member and at least a portion of the removal tool, so that the obstruction is captured between the expandable member and the removal tool, as the delivery tool is being removed from the vasculature to remove the removal tool and the obstruction from the vasculature, wherein the intermediate catheter is used to urge the expandable member to invert and/or fold over itself, in accordance with one or more embodiments of the present disclosure.

FIG. 1E illustrates a cross-sectional side view of the obstruction removal device of the obstruction removal system deployed within the vasculature, wherein the middle portion of the expandable member is folded over the distal end of the expandable member and at least a portion of the removal tool, so that the obstruction is captured between the expandable member and the removal tool, in accordance with one or more embodiments of the present disclosure.

FIG. 1F illustrates a cross-sectional side view of the obstruction removal device and the intermediate catheter of the obstruction removal system being pulled back through the guide catheter to remove the obstruction from the vasculature, in accordance with one or more embodiments of the present disclosure.

FIG. 3A illustrates a cross-sectional side view of the obstruction removal device of the obstruction removal system including a passive removal tool in a deployed (expanded) configuration, in accordance with one or more embodiments of the present disclosure.

FIG. 3B illustrates a cross-sectional side view of the obstruction removal device of the obstruction removal system including a passive removal tool in a deployed (expanded) configuration, wherein the passive removal tool is reinforced by an inner frame, in accordance with one or more embodiments of the present disclosure.

FIG. 4A illustrates a cross-sectional side view of the obstruction removal device of the obstruction removal system including an active removal tool in an undeployed (collapsed) configuration, in accordance with one or more embodiments of the present disclosure.

FIG. 4B illustrates a cross-sectional side view of the obstruction removal device of the obstruction removal system including an active removal tool in a deployed (expanded) configuration, in accordance with one or more embodiments of the present disclosure.

DETAILED DESCRIPTION

Figure 2A:
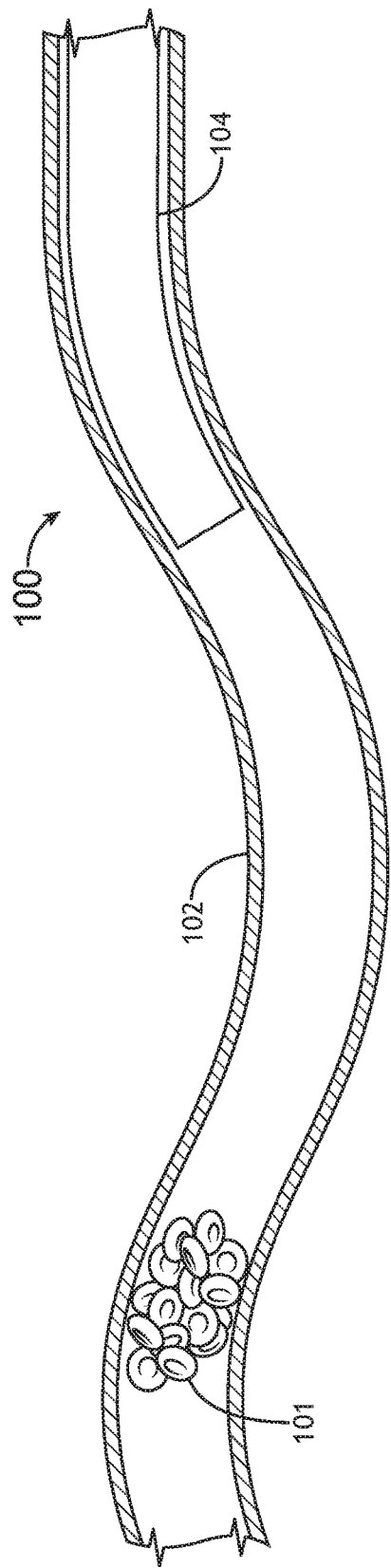
FIG. 2A illustrates a cross-sectional side view of a guide catheter of an obstruction removal system deployed within a vasculature, in accordance with one or more embodiments of the present disclosure.

Reference will now be made in detail to the subject matter disclosed, which is illustrated in the accompanying drawings. Referring generally to FIGS. 1A through 5C, an obstruction removal system is described, in particular, an obstruction removal system configured to selectively deploy a removal tool with an expandable member in a vasculature to reduce the risks associated with removal of an obstruction. The expandable member may be used to prevent the obstruction from dislodging from the removal tool and passing to a potentially more dangerous area (e.g. causing a total blockage, blocking a portion of a vital vasculature, etc.). In this regard, a physician may determine whether an obstruction is prone to risk and selectively deploy the removal tool with the expandable member.

FIGS. 1A through 1F illustrate one or more embodiments of an obstruction removal system 100. As shown in FIG. 1A, the obstruction removal system 100 includes a guide catheter 104 (e.g., any suitable guide catheter, aspiration catheter, or any other suitable tube) configured to be inserted through a vasculature 102 to a position proximate to an obstruction 101. Referring now to FIG. 1B, the obstruction removal system 100 further includes an obstruction removal device comprising a removal tool 110 and an expandable member 112 configured to be inserted through the guide catheter 104. For example, the removal tool 110 and the expandable member 112 may be coupled or formed on/near a distal end of a delivery tool 108 that is configured to be inserted through the guide catheter 104. In embodiments, the delivery tool 108 may be a guide wire or tube. In this regard, the removal tool 110 may be fixed to the distal end of the guide wire or tube, and the expandable member 112 may be fixed or slidably coupled to the guide wire or tube at a position near the removal tool 110.

In embodiments, the obstruction removal device (i.e., the removal tool 110 and the expandable member 112 on the delivery tool 108) may be at least partially housed within an intermediate catheter 106 (e.g., any suitable intermediate catheter, microcatheter, or any other suitable tube) during insertion. The intermediate catheter 106 may be used to contain and keep the removal tool 110 and the expandable member 112 from expanding within the guide catheter 104. This may provide one or more advantages, such as, but not limited to, reducing friction between the removal tool 110/expandable member 112 and the guide catheter 104, permitting the removal tool 110 and the expandable member 112 to be inserted through the distal opening of the guide catheter 104, and preventing the removal tool 110/expandable member 112 from prematurely engaging the obstruction 101.

FIG. 1B illustrates the obstruction removal device deployed within the vasculature 102 in proximity to an obstruction 101. The delivery tool 108 (e.g., a guide wire and/or tube) is configured to be inserted within the guide catheter 104 and disposed proximate to the obstruction 101 in the vasculature 102. For example, the delivery tool 108, carrying the end-mounted the removal tool 110 and the expandable member 112, may be fed through the guide catheter 104 using the intermediate catheter 106 to contain/sheathe the removal tool 110 and the expandable member 112 during their insertion.

Referring now to FIG. 1C, the intermediate catheter 106 may be configured to unsheathe the removal tool 110 and the expandable member 112 so that the removal tool 110 can engage the obstruction 101 in the vasculature 102. For example, after reaching a desired position within the vasculature 102, the intermediate catheter 106 may be pulled back (and/or the delivery tool 108 may be pushed forward relative to the intermediate catheter 106) to unsheathe the removal tool 110 and the expandable member 112 so that the removal tool 110 can engage the obstruction 101.

The removal tool 110 is configured to at least partially separate the obstruction 101 from the inner surface of the vasculature 102 (e.g., from the vessel wall). In embodiments, the removal tool 110 comprises a conical or umbrella-shaped section (e.g., a conical and/or umbrella shaped net-like structure or mesh) configured to at least partially surround the obstruction 101. In other embodiments, the removal tool 110 comprises a differently shaped net-like structure or mesh configured to at least partially surround the obstruction 101 (e.g., a semi-circular or cylindrical structure, or the like).

In embodiments where the delivery tool 108 comprises a guide wire disposed within a tube, the distal end of the removal tool 110 may be attached to the guide wire and another (mid) portion of the removal tool may be attached to the tube so that moving the guide wire independent of (e.g., relative to) the tube causes the removal tool 110 to expand or collapse, much like an umbrella. Additionally, or alternatively, the removal tool 110 may be formed from a shape memory and/or super elastic alloy (e.g., Nitinol) so that the removal tool 110 automatically expands when it is unsheathed. For example, the removal tool 110 may be guided past the obstruction 101, unsheathed, and then pulled back to scrape/scoop the obstruction 101 off the inner surface of the vasculature 102.

The expandable member 112 includes a distal end 114 that is fixedly or slidably coupled to the delivery tool 110 and a proximal end 116 that is slidably coupled to the delivery tool 110. The expandable member 112 may be positioned so that, during its deployment, the distal end 114 is located in between the removal tool 110 and the proximal end 116.

As shown in FIG. 1D, when the delivery tool 108 is withdrawn (e.g., pulled back into the guide catheter 104 and/or intermediate catheter 106), the proximal end 116 of the expandable member 112 may be configured to slide toward the distal end 114 of the expandable member 112, thereby causing the expandable member 112 to surround at least a portion of the obstruction 101 and the removal tool 110 so that the obstruction 101 is captured between the expandable member 112 and the removal tool 110. In embodiments, when the proximal end 116 of the expandable member 112 slides toward the distal end 114 of the expandable member 112 as a result of the delivery tool 108 being removed from the vasculature 102 to remove the removal tool 110 and the obstruction 101 from the vasculature 102, a middle portion 118 of the expandable member 112 is configured to fold over the distal end 114 of the expandable member 112 and at least a portion of the removal tool 110, so that the obstruction 101 is captured between the expandable member 112 and the removal tool 110. For example, when the delivery tool 108 is pulled back through the guide catheter 104 and/or intermediate catheter 106, the resulting friction between the middle portion 118 of the expandable member 112 and the inner surface of the vasculature 102 (e.g., as shown FIG. 1D-1), the guide catheter 104, or the intermediate catheter 106 may cause the middle portion of the expandable member 112 to fold over the removal tool 110 so that the obstruction 101 is captured between the expandable member 112 and the removal tool 110. Additionally, or alternatively, when the delivery tool 108 is pulled back through the guide catheter 104 and/or intermediate catheter 106, the resistance from fluid in the vasculature 102 may cause the middle portion of the expandable member 112 to fold over the removal tool 110 so that the obstruction 101 is captured between the expandable member 112 and the removal tool 110. Furthermore, as shown in FIG. 1D-2, in some embodiments, the intermediate catheter 106 (or guide catheter 104) may be used to urge the expandable member 112 to invert and/or fold over itself.

FIG. 1E illustrates the obstruction 101 captured between the expandable member 112 and the removal tool 110, as the delivery tool 108 is being withdrawn from the vasculature 102 to remove the removal tool 110 and the obstruction 101 from the vasculature 102. For example, the delivery tool 108 may be pulled back into the guide catheter 104 and/or intermediate catheter 106 to remove the obstruction 101 that is captured between the expandable member 112 and the removal tool 110 from the vasculature 102.

As shown in FIG. 1F, the intermediate catheter 106 with the delivery tool 108 and the obstruction 101 that is captured between the expandable member 112 and the removal tool 110 may be pulled back through the guide catheter 104 to remove the obstruction 101 from the vasculature 102. The delivery tool 108 with the obstruction removal device (including removal tool 110 and expandable member 112) and the obstruction 101 may be withdrawn through the intermediate catheter 106, as depicted in FIG. 1F. Alternatively, the delivery tool 108 with the obstruction 101 that is captured between the expandable member 112 and the removal tool 110 may be pulled directly through the guide catheter 104 (without use of an intermediate catheter 106).

FIGS. 2A through 2F illustrate another embodiment of the obstruction removal system 100, wherein the expandable member 112 has a distal end 114 coupled to the delivery tool 108 and a proximal end 116 that is configured to move freely. For example, the expandable member 112 may comprise a conical/umbrella-shaped net or mesh structure with one end fixedly or slidably coupled to the delivery tool 108 and one free/open end.

Figure 2B:
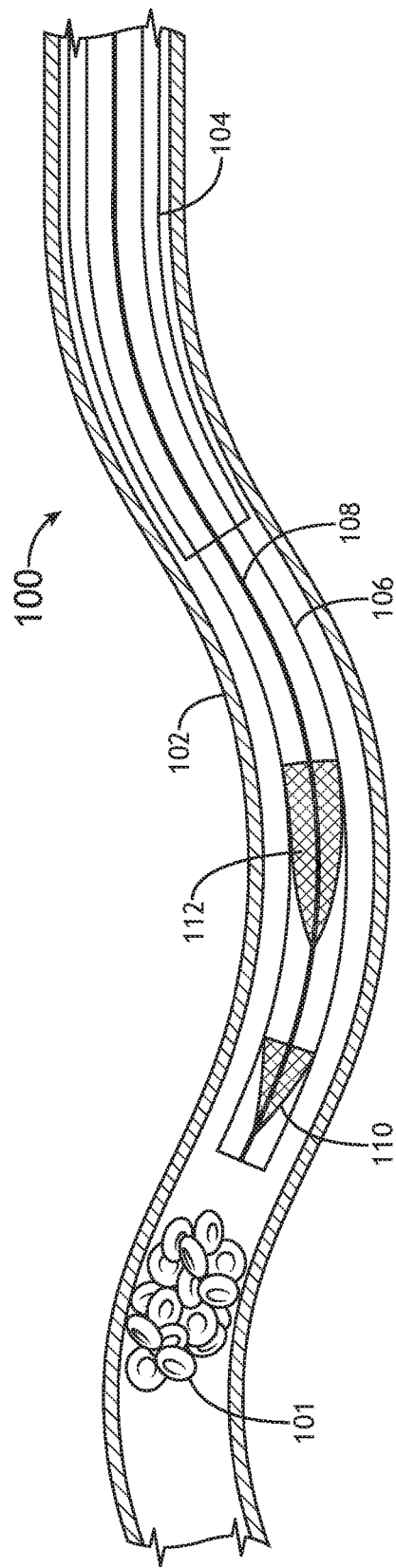
FIG. 2B illustrates a cross-sectional side view of an obstruction removal device of the obstruction removal system deployed through the guide catheter, wherein the obstruction removal device includes a removal tool and an expandable member attached to a delivery tool that is fed through the guide catheter using an intermediate catheter, in accordance with one or more embodiments of the present disclosure.
Figure 2C:
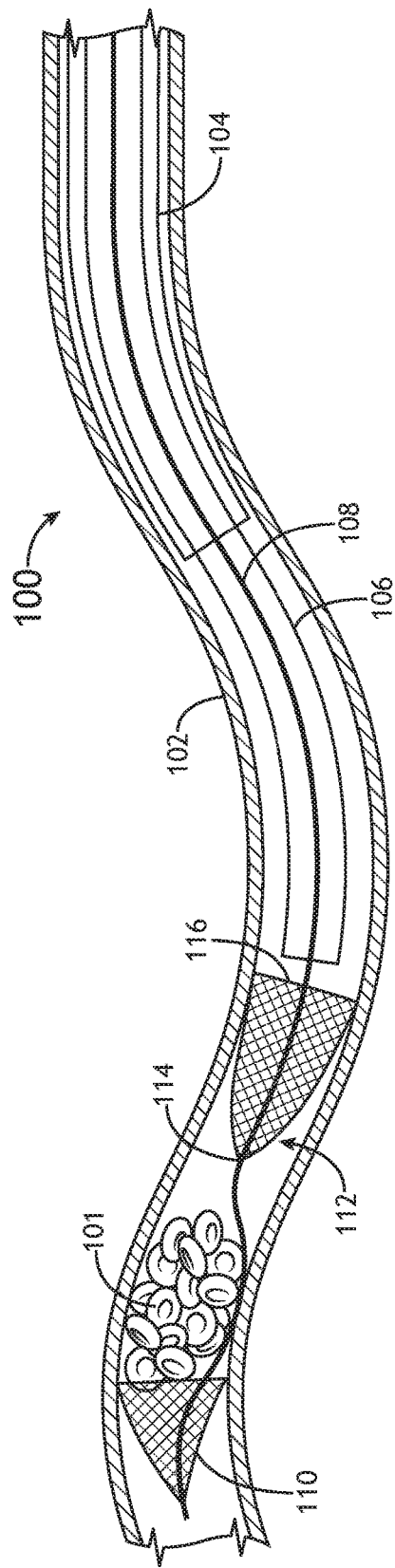
FIG. 2C illustrates a cross-sectional side view of the obstruction removal device of the obstruction removal system deployed within the vasculature, wherein the intermediate catheter is pulled back (and/or the delivery tool is pushed forward) to unsheathe the obstruction removal device so that the obstruction removal device can engage the obstruction with the removal tool to at least partially separate the obstruction from an inner surface of the vasculature, in accordance with one or more embodiments of the present disclosure.
Figure 2D:
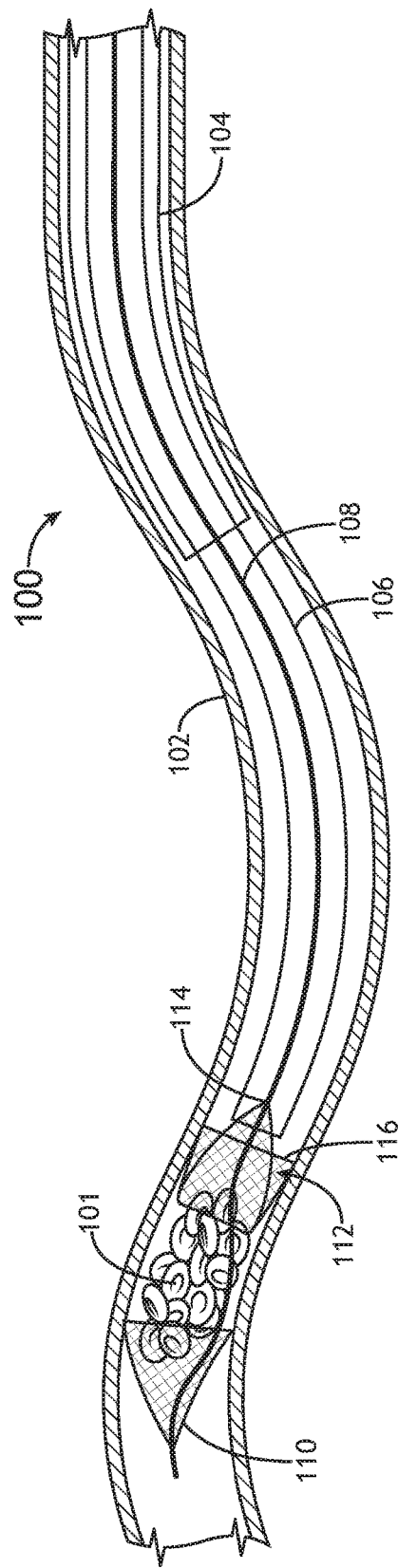
FIG. 2D illustrates a cross-sectional side view of the obstruction removal device of the obstruction removal system deployed within the vasculature, wherein a proximal end of the expandable member is being inverted and draped over the distal end of the expandable member and at least a portion of the removal tool, so that the obstruction is captured between the expandable member and the removal tool, as the delivery tool is being removed from the vasculature to remove the removal tool and the obstruction from the vasculature, in accordance with one or more embodiments of the present disclosure.

As shown in FIGS. 2B and 2C, when the obstruction removal device (i.e., the removal tool 110 and the expandable member 112 on the delivery tool 108) is being guided through the vasculature 102 to the obstruction 101, the expandable member 112 may be oriented so that the proximal end 116 of the expandable member 112 is facing away from the removal tool 110. Then, as shown in FIG. 2D, when the delivery tool 108 is withdrawn (e.g., pulled back into the guide catheter 104 and/or intermediate catheter 106), the proximal end 116 of the expandable member 112 may be configured to invert toward the distal end 114 of the expandable member 112, thereby causing the expandable member 112 to surround at least a portion of the obstruction 101 and the removal tool 110 so that the obstruction 101 is captured between the expandable member 112 and the removal tool 110. In embodiments, the proximal end 116 of the expandable member 112 is configured to invert and drape over the distal end 114 of the expandable member 112 and at least a portion of the removal tool 110 as the delivery tool 108 is withdrawn from the vasculature 102 to remove the removal tool 110 and the obstruction 101 from the vasculature 102. For example, when the delivery tool 108 is pulled back through the guide catheter 104 and/or intermediate catheter 106, the resulting friction between the proximal (i.e., free) end 116 of the expandable member 112 and the inner surface of the vasculature 102, the guide catheter 104, or the intermediate catheter 106 may cause the expandable member 112 to invert and drape over the removal tool 110 so that the obstruction 101 is captured between the expandable member 112 and the removal tool 110. Additionally, or alternatively, when the delivery tool 108 is pulled back through the guide catheter 104 and/or intermediate catheter 106, the resistance from fluid in the vasculature 102 may cause the expandable member 112 to invert and drape over the removal tool 110 so that the obstruction 101 is captured between the expandable member 112 and the removal tool 110.

Figure 2E:
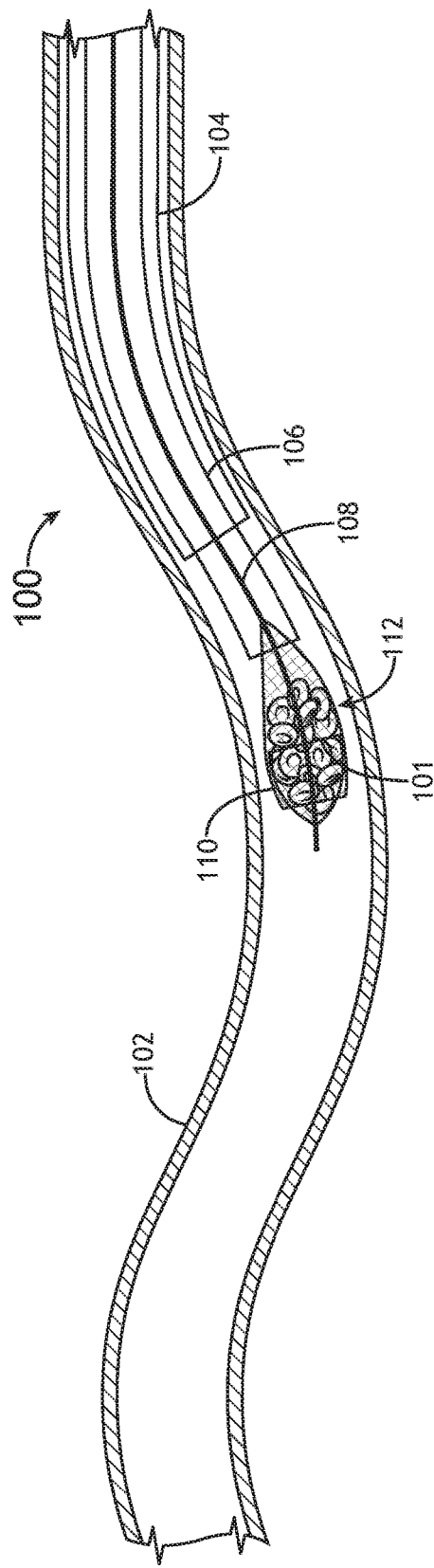
FIG. 2E illustrates a cross-sectional side view of the obstruction removal device of the obstruction removal system deployed within the vasculature, wherein the proximal end of the expandable member is inverted and draped over the distal end of the expandable member and at least a portion of the removal tool, so that the obstruction is captured between the expandable member and the removal tool, in accordance with one or more embodiments of the present disclosure.

FIG. 2E illustrates the obstruction 101 captured between the expandable member 112 and the removal tool 110, as the delivery tool 108 is being withdrawn from the vasculature 102 to remove the removal tool 110 and the obstruction 101 from the vasculature 102. For example, the delivery tool 108 may be pulled back into the guide catheter 104 and/or intermediate catheter 106 to remove the obstruction 101 that is captured between the expandable member 112 and the removal tool 110 from the vasculature 102.

Figure 2F:
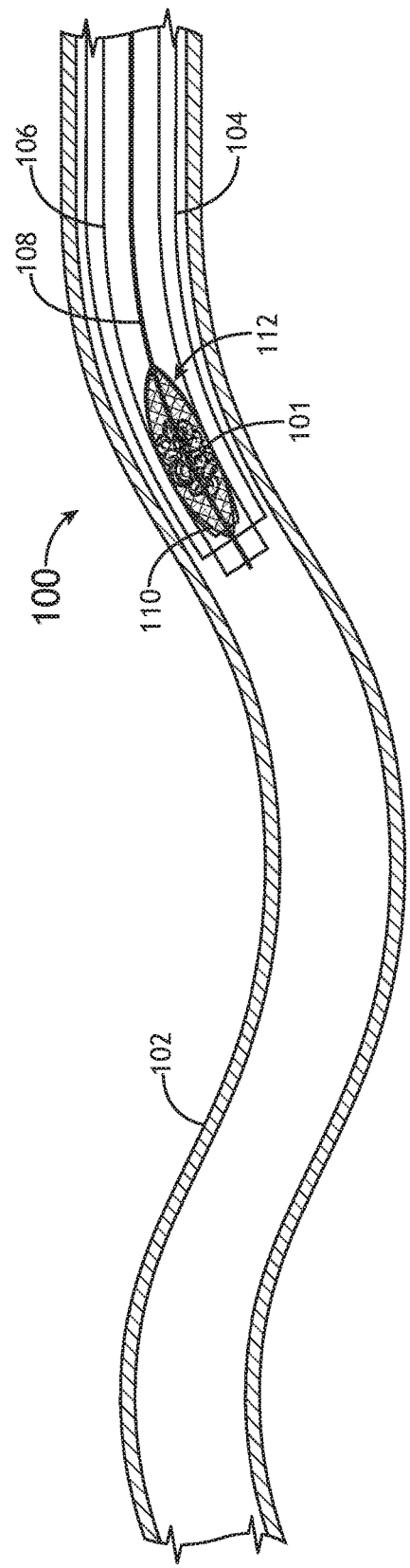
FIG. 2F illustrates a cross-sectional side view of the obstruction removal device and the intermediate catheter of the obstruction removal system being pulled back through the guide catheter to remove the obstruction from the vasculature, in accordance with one or more embodiments of the present disclosure.

As shown in FIG. 2F, the intermediate catheter 106 with the delivery tool 108 and the obstruction 101 that is captured between the expandable member 112 and the removal tool 110 may be pulled back through the guide catheter 104 to remove the obstruction 101 from the vasculature 102. The delivery tool 108 with the obstruction removal device (including removal tool 110 and expandable member 112) and the obstruction 101 may be withdrawn through the intermediate catheter 106, as depicted in FIG. 2F. Alternatively, the delivery tool 108 with the obstruction 101 that is captured between the expandable member 112 and the removal tool 110 may be pulled directly through the guide catheter 104 (without use of an intermediate catheter 106).

Referring now to FIGS. 3A through 5C, various embodiments of the removal tool 110 are shown and described. Embodiments of the removal tool 110 illustrated in FIGS. 3A through 5C may be employed with any embodiments of the obstruction removal system 100 illustrated in FIGS. 1A through 2F or otherwise described herein.

In embodiments, such as those illustrated in FIGS. 3A and 3B, the obstruction removal device may include a passive removal tool 110. In this regard, the removal tool 110 may be configured to expand upon deployment (e.g., unsheathing) from the intermediate catheter 106. The removal tool 110 may include a distal end 109 (e.g., tip coil) that is fixed to a distal end of the delivery tool 108 (e.g., delivery tube or wire) and a proximal end 111 that is fixed or slidably coupled to another portion of the delivery tool 108 such that an obstruction landing area 120 on the delivery tool 108 is defined between the proximal end 111 of the removal tool 110 and the distal end 114 of the expandable member 112. In some embodiments, the ends of the removal tool 110 and/or expandable member 112 comprise marker bands that are coupled to the delivery tool 108.

Figure 4C:
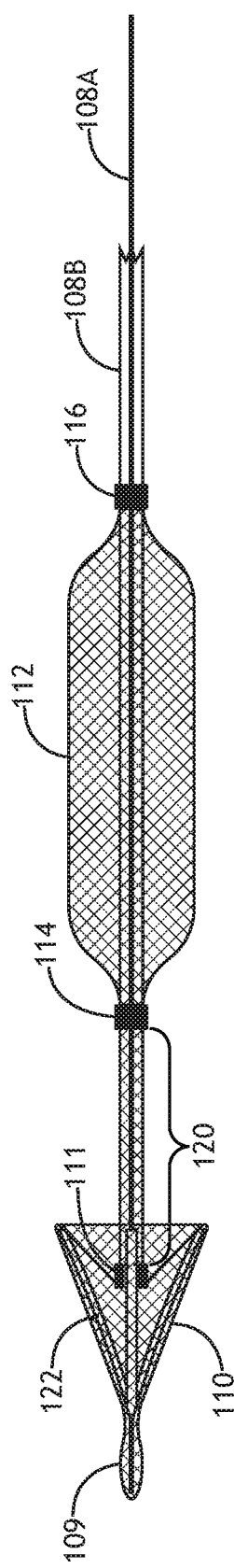
FIG. 4C illustrates a cross-sectional side view of the obstruction removal device of the obstruction removal system including an active removal tool in a deployed (expanded) configuration, wherein the active removal tool is reinforced by an inner frame, in accordance with one or more embodiments of the present disclosure.

FIGS. 4A through 4C illustrate embodiments of the obstruction removal device including an active removal tool 110. In this regard, the removal tool 110 may be selectively expanded or collapsed. For example, the removal tool 110 may be expanded or collapsed by actuating two portions of a delivery tool 108 (e.g., a delivery wire 108A and a delivery tube 108B) relative to one another. The removal tool 110 may include a distal end 109 (e.g., tip coil) that is fixed to a distal end of the delivery wire 108A and a proximal end 111 that is fixed to a distal end of the delivery tube 108B, either directly or via an obstruction landing area 120 between the proximal end 111 of the removal tool 110 and the distal end 114 of the expandable member 112 (as shown).

In embodiments, the expandable member 112 may be coupled to the delivery tube 108B such that the obstruction landing area 120 is defined between the proximal end 111 of the removal tool 110 and the distal end 114 of the expandable member 112. The obstruction landing area 120 may comprise a wire mesh portion that connects the removal tool 110 and the expandable member 112 together. In some embodiments, the expandable member 112 and the removal tool 110 may be portions of a continuous wire mesh structure.

The ends of the removal tool 110 and/or expandable member 112 may comprise marker bands that are coupled to respective portions of the delivery wire 108A and tube 108B. As shown in FIGS. 4A and 4B, respectively, the removal tool 110 may be collapsed by pushing the delivery wire 108A through the delivery tube 108B (or pulling the delivery tube 108B away from the distal end of the delivery wire 108A) and may expanded by pulling the delivery wire 108A through the delivery tube 108B (or pushing the delivery tube 108B toward the distal end of the delivery wire 108A).

Figure 5A:
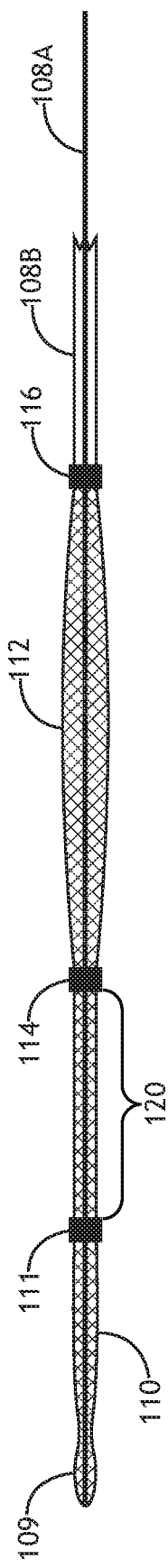
FIG. 5A illustrates a cross-sectional side view of the obstruction removal device of the obstruction removal system including an active removal tool in an undeployed (collapsed) configuration, in accordance with one or more embodiments of the present disclosure.
Figure 5B:
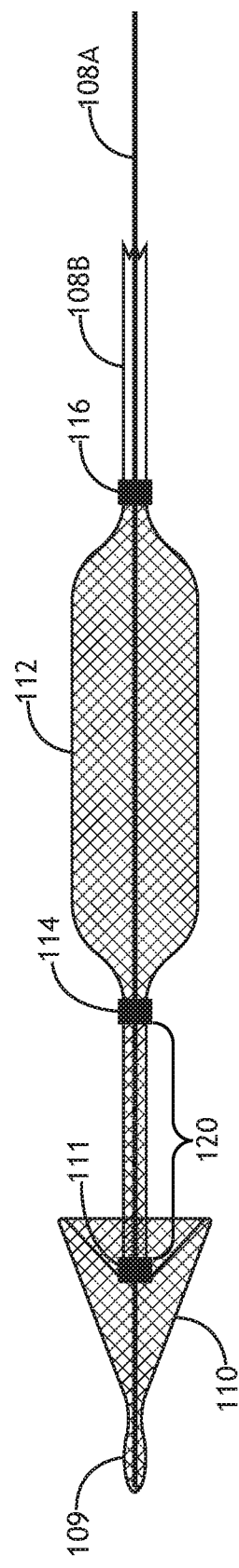
FIG. 5B illustrates a cross-sectional side view of the obstruction removal device of the obstruction removal system including an active removal tool in a deployed (expanded) configuration, in accordance with one or more embodiments of the present disclosure.
Figure 5C:
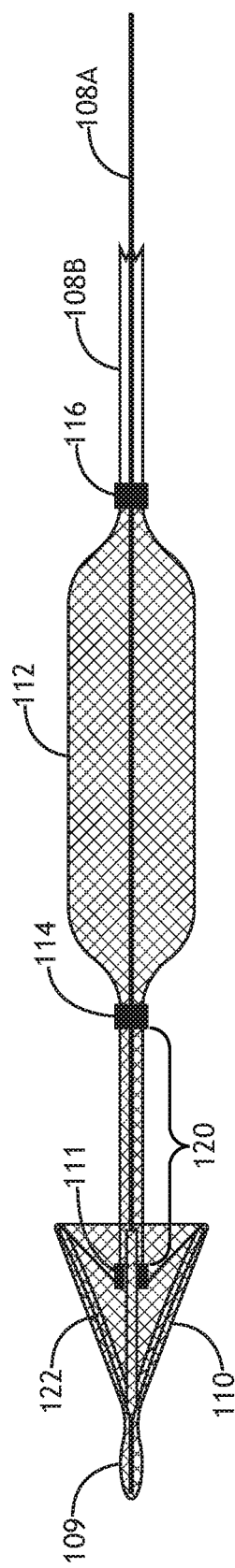
FIG. 5C illustrates a cross-sectional side view of the obstruction removal device of the obstruction removal system including an active removal tool in a deployed (expanded) configuration, wherein the active removal tool is reinforced by an inner frame, in accordance with one or more embodiments of the present disclosure.

FIGS. 5A through 5C illustrate embodiments of the obstruction removal device including an active removal tool 110 and an active expandable member 112. In this regard, the removal tool 110 and the expandable member 112 may be selectively expanded or collapsed. For example, the removal tool 110 may be expanded or collapsed by actuating two portions of a delivery tool 108 (e.g., a delivery wire 108A and a delivery tube 108B) relative to one another. The removal tool 110 may include a distal end 109 (e.g., tip coil) that is fixed to a distal end of the delivery wire 108A and a proximal end 111 that is connected to the distal end 114 of the expandable member 112 via an obstruction landing area 120 between the proximal end 111 of the removal tool 110 and the distal end 114 of the expandable member 112. The obstruction landing area 120 may comprise a wire mesh portion that connects the removal tool 110 and the expandable member 112 together. In some embodiments, the expandable member 112 and the removal tool 110 may be portions of a continuous wire mesh structure.

The ends of the removal tool 110 and/or expandable member 112 may comprise marker bands that are coupled to respective portions of the delivery wire 108A and tube 108B. As shown in FIGS. 5A through 5C, the proximal end 116 of the expandable member 112 may be coupled to a distal end of the delivery tube 108B so that pulling the delivery tube 108B back relative to the delivery wire 108A (or extending the delivery wire 108A forward relative to the delivery tube 108B) causes the removal tool 110 and the expandable member 112 to collapse; and conversely, pulling the delivery wire 108A back relative to the delivery tube 108B (or pushing the delivery tube 108B forward relative to the delivery wire 108A) causes the removal tool 110 and the expandable member 112 to expand.

As shown in FIGS. 3B, 4C, and 5C, in some embodiments, the removal tool 110 may include a support frame 122 (e.g., one or more rigid or semi-rigid structures) that provide structural reinforcement for the removal tool 110 when the removal tool 110 is in a deployed (i.e., expanded) configuration. The support frame 122 may be configured to collapse (e.g., fold toward the delivery tool 108) when the removal tool 110 is in a collapsed configuration. Additionally, or alternatively, the removal tool 110 may include non-uniform wire mesh. For example, the removal tool 110 structure may comprise thicker, stronger, and/or denser wire mesh toward the distal end 109 of the removal tool 110 to provide a stronger conical/funnel shaped structure when the removal tool 110 is deployed/expanded and thinner, weaker, and/or less dense wire mesh toward the proximal end 111 of the removal tool 110 to provide flexibility for the removal tool 110 to expand/collapse more easily.

In the embodiments illustrated in FIGS. 1A through 5C, or combinations thereof, the expandable member 112 may be configured to transition between contracted/collapsed and expanded states. The expandable member 112 may be configured to transition between the contracted and expanded states in any suitable way, including, but not limited to, unsheathing the expandable member 112 to allow expansion and sheathing/re-sheathing the expandable member 112 to induce contraction.

The expanded state may allow the expandable member 112 to surround at least a portion of the removal tool 110 and/or the obstruction 101. The contracted state may be suitable for insertion and removal of the obstruction removal device (including expandable member 112 and removal tool 110) through the guide catheter 104 and/or intermediate catheter 106. For example, when the expandable member 112 is in the collapsed/contracted state, after surrounding at least a portion of the removal tool 110 and/or the obstruction 101, the expandable member 112 and the removal tool 110 may be withdrawn through the guide catheter 104 and/or the intermediate catheter 106 to remove the obstruction 101 from the vasculature 102.

Benefits of surrounding at least a portion of the removal tool 110 and/or the obstruction 101 with the expandable member 112 may include, but are not limited to, smaller cross-sectional area, reduced friction on a vessel wall, reduced likelihood of catching on an opening of the guide catheter 104 and/or intermediate catheter 106, and reduced likelihood of obstruction dislodgement.

Referring generally to embodiments of the obstruction removal system 100 disclosed herein, the expandable member 112 may be configured to transition between a first configuration and a second configuration, or between a contracted state and an expanded state, in any number of ways, including, but not limited to, unsheathing (e.g., withdrawal of the intermediate catheter 106 or extension through the guide catheter 104), disengagement of locking members (e.g., wires, hooks, etc.) attached to the expandable member 112, use of shape memory alloys (e.g., Nitinol), or the like. It is envisioned that when the expandable member is in an expanded state, the expandable member may take up a substantial portion of the cross-section of the vasculature 102.

In embodiments, the expandable member 112, removal tool 110, and the obstruction 101 are withdrawn into the guide catheter 104 and removed from the vasculature 102. In some embodiments, the expandable member 112, removal tool 110, and the obstruction 101 may be further withdrawn into the intermediate catheter 106. The expandable member 112 may surround at least a portion of the obstruction 101 to prevent dislodging and may also assist in compressing the obstruction 101 into the guide catheter 104 and/or the intermediate catheter 106 (e.g., by tension, cinching, crimping, etc.).

Surrounding at least a portion of the removal tool 110 and/or obstruction 101 with the expandable member 112 may serve several functions including, but not limited to, reducing a likelihood that the removal tool 110 snags (e.g. on an inner surface/vessel wall of the vasculature 102 or an opening of the guide catheter 104), reducing a profile of the obstruction 101 for removal through the guide catheter 104 and/or intermediate catheter 106, and/or securing the obstruction 101 to prevent dislodgement from the removal tool 110.

In embodiments, the removal tool 110 and/or expandable member 112 may comprise a wire mesh. Such a wire mesh may include wires made of a flexible material (e.g. nitinol, cobalt chromium, polymer mesh (e.g., PET or nylon), or the like), where the wires (e.g. 16 to 288 or more wires), have a certain diameter (e.g. from 0.0005 inches to 0.0050 inches), and have certain material properties (e.g. strength, coefficient of friction with blood, resistance to plastic deformation, etc.) suitable for engaging the obstruction 101 and/or removal tool 110. The wire mesh can be can be single ply or multiple plies. Furthermore, the wire mesh may include various sets of wires (e.g. support wires with larger diameters, wires to engage a vessel wall, wires to engage a portion of the obstruction or obstruction removal device, radiopaque or radiodense wires, etc.).

Any number of the presently disclosed elements may be suitable for imaging by a non-invasive imaging technology (e.g. X-ray, CT scans, etc.). For instance, the guide catheter 104, intermediate catheter 106, delivery tool 108, removal tool 110, expandable member 112, and/or any additional components may comprise radiodense or radiopaque material (e.g. titanium, tungsten, barium sulfate, zirconium oxide, Drawn Filled Tube (DFT), or the like) suitable for insertion in a human body. In some embodiments, the removal tool 110 and the expandable member 112 are both portions of a common wire mesh structure formed from a radiodense or radiopaque material (e.g. DFT).

It is to be understood that any number of components of the obstruction removal system 100 may be attached by any suitable means including, but not limited to, welding, adhesive, mechanical fastening, interference fittings, etc. For example, the delivery tool 108 may be attached to the removal tool 110 and/or expandable member 112 by such means. Alternatively, or additionally, two or more of the components may be portions of a common structure (e.g., a common mold or print).

It is envisioned that there may be multiple orders in which one or more devices of the obstruction removal system 100 are deployed. Factors for determining an order may include, but are not limited to, vasculature properties (e.g. vasculature size, vasculature geometries, branches of the vasculature, vasculature wall strength, etc.), blood pressure, blood flow direction, duration of operation (i.e. does patient require a reduced operating time for safety concerns), size of obstruction, or the configuration of the obstruction removal device.

Referring generally to FIGS. 1A through 5C, a method of removing an obstruction from a vasculature 102 may include, but is not limited to, the steps of: deploying the guide catheter 104 through the patient's vasculature 102 to a position near the obstruction 101; extending the delivery tool 108 with the end-mounted removal tool 110 through the guide catheter 104 so that the distal end of the delivery tool 108 is disposed proximate to the obstruction 101 in the vasculature 102 (with/without the use of the intermediate catheter 106); removing at least a portion of the obstruction 101 in the vasculature 102 by at least partially separating the obstruction 101 from an inner surface of the vasculature 102 with the removal tool 110; and surrounding at least a portion of the obstruction 101 and the removal tool 110 with the expandable member 112, wherein the proximal end 116 of the expandable member 112 is configured to invert or slide toward the distal end 114 of the expandable member 112, so that the obstruction 101 is captured between the expandable member 112 and the removal tool 110, when the delivery tool 108 is withdrawn from the vasculature 102 to remove the removal tool 110 and the obstruction 101 from the vasculature 102.

It is to be understood that implementations of the methods disclosed herein may include one or more of the steps described herein. Further, such steps may be carried out in any desired order and, in some implementations, two or more of the steps may be carried out simultaneously with one another. Two or more of the steps disclosed herein may be combined in a single step, and in some implementations., one or more of the steps may be carried out as two or more sub-steps. Further, other steps or sub-steps may be carried in addition to, or as substitutes to one or more of the steps disclosed herein.

It is also to be understood that usage of terminology in the present disclosure is not intended to be limiting. For example, as used herein, an "obstruction" may refer to any vascular obstruction, including but not limited to, a blood clot, plaque (e.g. fat, cholesterol, etc.), internal structure/growth, foreign object, or the like.

Although the technology has been described with reference to the embodiments illustrated in the attached drawing figures, equivalents may be employed and substitutions made herein without departing from the scope of the technology as recited in the claims. Components illustrated and described herein are merely examples of a device and components that may be used to implement the embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. An obstruction removal system, comprising:
a guide catheter configured to be inserted within a vasculature;
a delivery tool having a distal end configured to be inserted within the guide catheter and disposed proximate to an obstruction in the vasculature; and
a continuous wire mesh structure coupled to the delivery tool, wherein respective portions of the continuous wire mesh structure form:
a removal tool disposed at the distal end of the delivery tool and configured to at least partially separate the obstruction from an inner surface of the vasculature, wherein the removal tool comprises a conical or umbrella-shaped section configured to at least partially surround the obstruction, and wherein the removal tool includes an inner support frame configured to structurally reinforce the removal tool when the removal tool is in a deployed configuration;

an expandable member coupled to the delivery tool, the expandable member including a proximal end that is free or slidably coupled to the delivery tool, wherein the proximal end of the expandable member is configured to invert or slide toward a distal end of the expandable member, thereby causing the expandable member to surround at least a portion of the obstruction and the removal tool so that the obstruction is captured between the expandable member and the removal tool, when the delivery tool is withdrawn from the vasculature to remove the removal tool and the obstruction from the vasculature; and an obstruction landing area between the removal tool and the expandable member, wherein the removal tool, the expandable member, and the obstruction landing area are separated by marker bands that are coupled to the delivery tool.

2. The obstruction removal system of claim 1, wherein the distal end of the expandable member is fixedly or slidably coupled to the delivery tool.

3. The obstruction removal system of claim 1, wherein the proximal end of the expandable member is slidably coupled to the delivery tool and is configured to slide toward the distal end of the expandable member when the delivery tool is withdrawn from the vasculature to remove the removal tool and the obstruction from the vasculature, and wherein a middle portion of the expandable member is configured to fold over the distal end of the expandable member and at least a portion of the removal tool, so that the obstruction is captured between the expandable member and the removal tool, when the proximal end of the expandable member slides toward the distal end of the expandable member as the delivery tool is withdrawn from the vasculature to remove the removal tool and the obstruction from the vasculature.

4. The obstruction removal system of claim 1, wherein the proximal end of the expandable member is free and is configured to invert and drape over the distal end of the expandable member and at least a portion of the removal tool, so that the obstruction is captured between the expandable member and the removal tool, when the delivery tool is withdrawn from the vasculature to remove the removal tool and the obstruction from the vasculature.

5. The obstruction removal system of claim 1, further comprising:
an intermediate catheter configured to sheathe the removal tool and the expandable member while the delivery tool is inserted within the guide catheter and guided into the vasculature.

6. The obstruction removal system of claim 5, wherein the intermediate catheter is further configured to unsheathe the removal tool and the expandable member to allow the removal tool to at least partially separate the obstruction from the inner surface of the vasculature.

7. The obstruction removal system of claim 1, wherein the delivery tool comprises at least one of a guide wire or a tube.

8. An obstruction removal device, comprising:
a continuous wire mesh structure coupled to a delivery tool, wherein respective portions of the continuous wire mesh structure form:
a removal tool disposed at a distal end of the delivery tool and configured to at least partially separate an obstruction from an inner surface of a vasculature, wherein the removal tool comprises a conical or umbrella-shaped section configured to at least partially surround the obstruction, and wherein the removal tool includes an inner support frame configured to structurally reinforce the removal tool when the removal tool is in a deployed configuration;

an expandable member coupled to the delivery tool, the expandable member including a proximal end that is free or slidably coupled to the delivery tool, wherein the proximal end of the expandable member is configured to invert or slide toward a distal end of the expandable member, thereby causing the expandable member to surround at least a portion of the obstruction and the removal tool so that the obstruction is captured between the expandable member and the removal tool when the delivery tool is withdrawn from the vasculature to remove the removal tool and the obstruction from the vasculature; and an obstruction landing area between the removal tool and the expandable member, wherein the removal tool, the expandable member, and the obstruction landing area are separated by marker bands that are coupled to the delivery tool.

9. The obstruction removal device of claim 8, wherein the distal end of the expandable member is fixedly or slidably coupled to the delivery tool.

10. The obstruction removal device of claim 8, wherein the proximal end of the expandable member is slidably coupled to the delivery tool and is configured to slide toward the distal end of the expandable member when the delivery tool is withdrawn from the vasculature to remove the removal tool and the obstruction from the vasculature, and wherein a middle portion of the expandable member is configured to fold over the distal end of the expandable member and at least a portion of the removal tool, so that the obstruction is captured between the expandable member and the removal tool, when the proximal end of the expandable member slides toward the distal end of the expandable member as the delivery tool is withdrawn from the vasculature to remove the removal tool and the obstruction from the vasculature.

11. The obstruction removal device of claim 8, wherein the proximal end of the expandable member is free and is configured to invert and drape over the distal end of the expandable member and at least a portion of the removal tool, so that the obstruction is captured between the expandable member and the removal tool, when the delivery tool is withdrawn from the vasculature to remove the removal tool and the obstruction from the vasculature.

* * * * *